(12) United States Patent
Lossing et al.

(10) Patent No.: US 6,528,248 B2
(45) Date of Patent: *Mar. 4, 2003

(54) PROCESSING TECHNOLOGY FOR LCM SAMPLES

(75) Inventors: Ann Bennett Lossing, Capitola, CA (US); Sherrie L. Ransom, San Francisco, CA (US); Steven T. Kunitake, San Carlos, CA (US); Robert H. Reamey, Palo Alto, CA (US); David F. Head, Los Gatos, CA (US); Hala Al-Shawany, Mountain View, CA (US)

(73) Assignee: Arcturus Engineering, Inc., Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 65 days.

(21) Appl. No.: 09/562,495

(22) Filed: May 1, 2000

(65) Prior Publication Data

US 2002/0132222 A1 Sep. 19, 2002

Related U.S. Application Data

(60) Provisional application No. 60/131,863, filed on Apr. 29, 1999.

(51) Int. Cl.$^7$ ................................................. A01G 5/06
(52) U.S. Cl. ............................................ 435/4; 427/4
(58) Field of Search .................................. 435/4; 427/4

(56) References Cited

U.S. PATENT DOCUMENTS

| | | |
|---|---|---|
| 3,680,947 A | 8/1972 | Wanesky |
| 3,705,769 A | 12/1972 | Johannsmeier |
| 3,836,231 A | 9/1974 | Cole, Jr. |
| 3,848,962 A | 11/1974 | Nelson |
| 3,939,019 A | 2/1976 | Pickett |
| 4,205,059 A | 5/1980 | von Hagens |
| 4,210,384 A | 7/1980 | Meyer et al. |
| 4,303,866 A | 12/1981 | Porro et al. |
| 4,333,983 A | 6/1982 | Allen |
| 4,436,385 A | 3/1984 | Fischer et al. |

(List continued on next page.)

FOREIGN PATENT DOCUMENTS

| | | |
|---|---|---|
| CH | 566 015 | 8/1975 |
| DE | 196 03 996 | 8/1997 |
| EP | 0 409 550 A1 | 1/1991 |
| WO | WO 91/07683 A1 | 5/1991 |
| WO | WO 94/02646 A1 | 2/1994 |
| WO | WO 95/23960 | 9/1995 |
| WO | WO 95/30919 | 11/1995 |
| WO | WO 97/13838 A1 | 4/1997 |
| WO | WO 98/35215 | 8/1998 |
| WO | WO 98/35216 | 8/1998 |
| WO | WO 99/00658 | 1/1999 |
| WO | WO 99/09390 A1 | 2/1999 |
| WO | WO 99/17094 | 4/1999 |
| WO | WO 99/19341 | 4/1999 |
| WO | WO 99/39176 | 8/1999 |
| WO | WO 99/45094 | 9/1999 |
| WO | WO 00/06992 | 2/2000 |
| WO | WO 00/34756 | 6/2000 |
| WO | WO 00/34757 | 6/2000 |
| WO | WO 00/49410 A1 | 8/2000 |
| WO | WO 00/49410 A3 | 8/2000 |
| WO | WO 00/66994 | 11/2000 |
| WO | WO 00/68662 A1 | 11/2000 |
| WO | WO 00/68662 A3 | 11/2000 |
| WO | WO 01/33190 A2 | 5/2001 |

OTHER PUBLICATIONS

Allred, C. D. and Mohsin, S. K. (2000). "Biological Features of Human Premalignant Brest Disease," Chapter 24 In *Disease of the Breast*, 2nd ed., J. R. Harris, ed., Lippicott Williams & Wilkins: Philadelphia, pp. 355–366.

Ashkin, A. and Dziedzic, J.M. (1989). "Internal Cell Manipulation Using Infrared Laser Traps," *Proc. Natl. Acad. Sci. USA* 86:7914–7918.

Bentley–Lawrence, J. et al. (1988). "Sensitive, High–Resolution Chromatin and Chromosome Mappin In Situ: Presence and Orientation of Two Closely Integrated Copies of EBV in a Lymphoma Line," *Cell* 52:51–61.

Bonner, R. F. et al. (Nov. 21, 1997). "Laser Capture Microdissection: Molecular Analysis of tissue," *Science* 278(5342):1481 and 1483.

Brignole, E. (2000). "Laser–Capture Microdissection," pp. 1–4, located at only 3 pages <<http://pubs.acs.org/subscribe/journals/mdd/v03/i09/html/toolbox.html1≦≦ from *Modern Drug Discovery*, 3(9):69–70, No Mention of Magazine.

Chu, S. S. et al. (2000). "Laser Capture Microdissection: Applications in Cancer Research," *Biomedical Product* 251p58:1–3.

Chui, G. (1999). "The Ecosystems Within" Section F, Science & Technology *San Jose Mercury News* pp. 1–5.

Emmert–Buck, M. R. et al. (1996). "Laser Capture Microdissection," *Science* 274:998–1001.

Friend, T. (1997). "Microdissection on Breakthrough Lets Scientist Isolate Those Involved in Tumor Growth," Printed in *USA Today* Newspaper, Science Section, 2 pages.

(List continued on next page.)

Primary Examiner—Christopher R. Tate
Assistant Examiner—Kailash C. Srivastava
(74) Attorney, Agent, or Firm—Morrison & Foerster LLP (57) ABSTRACT

Systems and methods are described for barriers on laser capture microdissection samples. A method of processing a biological sample for laser capture microdissection, includes: providing the biological sample; and applying a substance to the biological sample so as to provide a barrier between the biological sample and a surrounding environment. The systems and methods provide advantages because non-specific pick-up is reduced, visualization is improved, sample degradation is reduced, and contamination is reduced.

19 Claims, 6 Drawing Sheets

U.S. PATENT DOCUMENTS

| | | |
|---|---|---|
| 4,508,435 A | 4/1985 | Graham et al. |
| 4,509,834 A | 4/1985 | Hodgson |
| 4,538,885 A | 9/1985 | Graham et al. |
| 4,552,033 A | 11/1985 | Märzhäuser |
| 4,600,282 A | 7/1986 | Yamamura et al. |
| 4,614,431 A | 9/1986 | Komeyama |
| 4,624,915 A | 11/1986 | Schindler et al. |
| 4,627,009 A | 12/1986 | Holmes et al. |
| 4,629,687 A | 12/1986 | Schindler et al. |
| 4,673,261 A | 6/1987 | Hunt et al. |
| 4,684,781 A | 8/1987 | Frish et al. |
| 4,702,565 A | 10/1987 | Schilling et al. |
| 4,731,530 A | 3/1988 | Mikan |
| 4,807,984 A | 2/1989 | Kurimura et al. |
| 4,824,229 A | 4/1989 | Narita et al. |
| 4,836,667 A | 6/1989 | Ozeki |
| 4,852,985 A | 8/1989 | Fujihara et al. |
| 4,856,873 A | 8/1989 | Kleinberg |
| 4,871,245 A | 10/1989 | Ishikawa et al. |
| 4,920,053 A | 4/1990 | Inoue et al. |
| 4,923,294 A | 5/1990 | Courtenay |
| 4,954,715 A | 9/1990 | Zöld |
| 4,964,708 A | 10/1990 | Mason |
| 4,987,006 A | 1/1991 | Williams et al. |
| 4,992,660 A | 2/1991 | Kobayashi |
| 5,017,428 A | 5/1991 | Mecke et al. |
| 5,029,791 A | 7/1991 | Ceccon et al. |
| 5,057,689 A | 10/1991 | Nomura et al. |
| 5,077,620 A | 12/1991 | Mauro |
| 5,089,909 A | 2/1992 | Kleinberg |
| 5,103,338 A | 4/1992 | Crowley et al. |
| 5,126,877 A | 6/1992 | Biber |
| 5,143,552 A | 9/1992 | Moriyama |
| 5,162,941 A | 11/1992 | Favro et al. |
| 5,165,297 A | 11/1992 | Krueger |
| 5,173,802 A | 12/1992 | Heller |
| 5,173,803 A | 12/1992 | Heller |
| 5,202,230 A | 4/1993 | Kamentsky |
| 5,225,326 A | 7/1993 | Bresser et al. |
| 5,253,110 A | 10/1993 | Ichihara et al. |
| 5,262,891 A | 11/1993 | Nakasato |
| 5,263,384 A | 11/1993 | Suzuki |
| 5,280,384 A | 1/1994 | Shibasaki |
| 5,288,996 A | 2/1994 | Betzig et al. |
| 5,296,291 A | 3/1994 | Mueller |
| 5,296,963 A | 3/1994 | Murakami et al. |
| 5,298,963 A | 3/1994 | Moriya et al. |
| 5,312,393 A | 5/1994 | Mastel |
| 5,323,009 A | 6/1994 | Harris |
| 5,337,178 A | 8/1994 | Kung et al. |
| 5,345,333 A | 9/1994 | Greenberg |
| 5,357,366 A | 10/1994 | Marchlenski |
| 5,359,417 A | 10/1994 | Müller et al. |
| 5,367,401 A | 11/1994 | Saulietis |
| 5,378,675 A | 1/1995 | Takeyama et al. |
| 5,386,112 A | 1/1995 | Dixon |
| 5,393,647 A | 2/1995 | Neukermans et al. |
| 5,403,970 A | 4/1995 | Aoki |
| 5,412,503 A | 5/1995 | Nederlof |
| 5,420,716 A | 5/1995 | Fukaya |
| 5,434,703 A | 7/1995 | Morizumi |
| 5,450,233 A | 9/1995 | Yamamoto et al. |
| 5,455,420 A | 10/1995 | Ho et al. |
| 5,468,967 A | 11/1995 | Chan et al. |
| 5,471,260 A | 11/1995 | Luce et al. |
| 5,479,252 A | 12/1995 | Worster et al. |
| 5,492,837 A | 2/1996 | Naser-Kolahzadeh et al. |
| 5,492,861 A | 2/1996 | Opower |
| 5,504,366 A | 4/1996 | Weiss et al. |
| 5,506,725 A | 4/1996 | Koike et al. |
| 5,510,615 A | 4/1996 | Ho et al. |
| 5,517,353 A | 5/1996 | Ikoh et al. |
| 5,531,997 A | 7/1996 | Cochrum |
| 5,532,128 A | 7/1996 | Eggers et al. |
| 5,532,476 A | 7/1996 | Mikan |
| 5,532,873 A | 7/1996 | Dixon |
| 5,535,052 A | 7/1996 | Jörgens |
| 5,536,941 A | 7/1996 | Swann |
| 5,537,863 A | 7/1996 | Fujiu et al. |
| 5,541,064 A | 7/1996 | Bacus et al. |
| 5,552,928 A | 9/1996 | Furuhashi et al. |
| 5,556,790 A | 9/1996 | Pettit |
| 5,557,456 A | 9/1996 | Garner et al. |
| 5,558,329 A | 9/1996 | Liu |
| 5,559,329 A | 9/1996 | Joseph et al. |
| 5,578,832 A | 11/1996 | Trulson et al. |
| 5,587,748 A | 12/1996 | Luce et al. |
| 5,587,833 A | 12/1996 | Kamentsky |
| 5,598,888 A | 2/1997 | Sullivan et al. |
| 5,602,674 A | 2/1997 | Weissman et al. |
| 5,619,035 A | 4/1997 | Weiss et al. |
| 5,621,207 A | 4/1997 | O'Mara |
| 5,631,734 A | 5/1997 | Stern et al. |
| 5,638,206 A | 6/1997 | Sumiya et al. |
| 5,659,421 A | 8/1997 | Rahmel et al. |
| 5,665,582 A | 9/1997 | Kausch et al. |
| 5,707,801 A | 1/1998 | Bresser et al. |
| 5,723,290 A | 3/1998 | Eberwine et al. |
| 5,728,527 A | 3/1998 | Singer et al. |
| 5,751,839 A | 5/1998 | Drocourt et al. |
| 5,759,781 A | 6/1998 | Ward et al. |
| 5,817,462 A | 10/1998 | Garini et al. |
| 5,843,644 A | 12/1998 | Liotta et al. |
| 5,843,657 A | 12/1998 | Liotta et al. |
| 5,859,699 A | 1/1999 | Baer et al. |
| 5,985,085 A | 11/1999 | Baer et al. |
| 6,010,888 A | 1/2000 | Liotta et al. |
| 6,100,051 A | 8/2000 | Goldstein et al. |
| 6,157,446 A | 12/2000 | Baer et al. |
| 6,184,973 B1 | 2/2001 | Baer et al. |
| 6,204,030 B1 | 3/2001 | Liotta et al. |
| 6,215,550 B1 | 4/2001 | Baer et al. |
| 6,251,467 B1 | 6/2001 | Liotta et al. |
| 6,251,516 B1 | 6/2001 | Bonner et al. |
| 6,277,648 B1 | 8/2001 | Colpan |
| 2001/0031481 A1 | 10/2001 | Liotta et al. |

OTHER PUBLICATIONS

Fukui, K. et al. (Jun. 1992). "Microdissection of Plant Chromosomes by Argon–Ion Laser Beam," *Theoretical & Applied Genetics* 84:787–791.

Goldstein, S. R. et al. (1998). "Thermal Modeling of Laser Capture Microdessection," *Appllied Optics* 37(31):7378–7391.

Goldsworthy, S. M. et al. (1999). "Effects of Fixation on RNA Extraction and Amplification from Laser Capture Microdissected Tissue" *Molecular Carcinogenesis* 25:86–91.

Harlow and Lane, eds. (1988). *Antibodies: A Laboratory Manual* Cold Spring Harbor, New York: pp. iii–ix (Table of Contents Only).

Heng, H.H.Q. et al. (1992). "High–Resolution Mapping of Mammalian Genes by *In Situ* Hybridization to Free Chromatin," *Proc. Natl. Acad. Sci. USA* 89:9509–9513.

Isenberg, G. et al. (1976). "Cell Surgery by Laser Micro-–Dissection: a Preparative Method," *J. Microsc.* 107(Pt 1):19–24.

Jiménez, C. R. et al. (1994). "Neuropeptide expression and processing as revealed by direct matrix–assisted laser desorption ionization mass spectrometry of single neurons," *Journal of Neurochemistry* 62(1):404–407.

Kubo, Y. et al. (1995). "Early Detection of Knudson's Two–Hits in Preneoplastic Renal Cells of the Eker Rat Model by the Laser Microdissection Procedure," *Cancer Research* 55(5):989–990.

Kuska, B. (1996). "New Aim–and–Shoot Technique Speeds up Cell Analysis," *J. Natl. Cancer Inst.* 88(23):1708–1709.

Lewis, R. (1998). "Laser Aids Alzheimer's Study," *Biophotonics International* pp. 40–41.

Lichter, P. et al. (1990). "High–Resolution Mapping of Human Chromosome 11 by *In Situ* Hybridization with Cosmid Clones," *Science* 247:64–69.

Manuelidis, L. et al. (1982). "High–Resolution Mapping of Satellite DNA Using Biotin–Labeled DNA Probes," *The J. Cell. Biol.* 95:619–625.

Meier–Ruge, W. et al. (1976). "The Laser in the Lowry Technique for Microdissection of Freeze–Dried Tissue Slices," *Histochemical Journal* 8:387–401.

Relman, D. A. (1999). "The Search for Unrecognized Pathogens", *Science* 284: 1308–1310.

Schindler, M. (1998). "Select, microdissect & eject," *Nature Biotechnology* 16:719–720.

Schindler, M. et al. (1985). "Automated Analysis & Survival Selection of Anchorage–Dependent Cells under Normal Growth Conditions," *Cytometry* 6(4):368–374.

Schütze, K. and Lahr, Georgia (Aug. 1998). "Identification of Expressed Genes by Laser–Mediated Manipulation of Single Cells," *Nature Biotechnology* 16:737–742.

van den Engh, Ger et al. (1992). "Estimating Genomic Distance from DNA Sequence Location in Cell Nuclei by a Random Walk Model," *Science* 257:1410–1412.

Veigel, Claudia et al. (1994). "New Cell Biological Applications of the Laser Microbeam Technique: the Microdissection and Skinning of Muscle Fibers and the Perforation and Fusion of Sacrolemma Vesicles," *European Journal of Cell Biology* 63:140–148.

Simone, N.L. et al. (1998). "Laser–Capture Microdissection: Opening the Microscopic Frontier to Molecular Analysis," *Trends In Genetics* 14(7):272–276.

PROCESSING TECHNOLOGY FOR LCM SAMPLES

CROSS-REFERENCE TO RELATED APPLICATION

This application is a continuation-in-part under 35 U.S.C. §120 of copending U.S. Ser. No. 60/131,863, filed Apr. 29, 1999, now pending, the entire contents of which are hereby incorporated herein by reference as if fully set forth herein.

BACKGROUND OF THE INVENTION

1. Field of the Invention

The invention relates generally to the field of laser capture microdissection (LCM). More particularly, the invention relates to providing a biological sample with a polymer barrier prior to laser capture microdissection.

2. Discussion of the Related Art

LCM is a process by which cells and portions of biological tissue samples are acquired directly from tissue sections mounted on glass slides or other solid surfaces. The process involves placing a Capsure™ device, containing a thin-film polymer, onto the tissue section. Once the cells or tissue portions of interest (tissue targets) are located in the sample, a laser is focused over the tissue targets. When the laser is fired, the thin-film located directly above the tissue targets melts, flows down and adheres to the tissue targets. The Capsure™ device, holding the adhered tissue targets, is then removed from the tissue sample. The tissue targets are now stabilized on the Capsure™ device and ready for molecular analysis.

Currently, when Capsure™ devices make contact with a tissue section during LCM, the total working area of the Capsure™ device touches the surface of the tissue section. Due to the friable nature of tissue sections, loose material (whole cell or macromolecular) is likely to adhere to the surface of the Capsure™ device during LCM. This is known as non-specific transfer. Since LCM sample recovery involves extraction of the material on the surface of a Capsure™ device, any non-specific material transferred during LCM can cause sample contamination and adversely affect the quality and accuracy of downstream analyses.

Heretofore, the requirement of reducing or eliminating non-specific transfer during LCM has not been fully met. What is needed is a solution that addresses this requirement. The invention is directed to meeting this requirement, among others.

SUMMARY OF THE INVENTION

The principal goal of the invention is to satisfy the above-discussed requirement of reduction or elimination of non-specific transfer during LCM. It was reasoned that by applying a protective barrier or coating to biological tissue sections prior to LCM, loosely adhered tissue would be retained beneath the barrier, whereas tissue targets adhered to the melted polymer would easily be removed with the Capsure™ device. Another goal of the invention is to improve visualization of the sample during LCM. Another goal of the invention is to stabilize and retard degradation of biological samples being used for LCM or other types of biological analysis. Another goal of the invention is to reduce contamination of biological samples during storage before or after LCM.

One embodiment of the invention is based on a method of processing a biological sample for laser capture microdissection, comprising: providing the biological sample; and applying a substance to the biological sample so as to provide a barrier between the biological sample and a surrounding environment. Another embodiment of the invention is based on an article of manufacture, comprising: a biological sample that is to undergo laser capture microdissection; and a barrier coupled to at least a portion of said biological sample. Another embodiment of the invention is based on an article of manufacture, comprising: a portion of a biological sample that has undergone laser capture microdissection; and a barrier coupled to said portion of said biological sample. Another embodiment of the invention is based on a composition to process a biological sample for laser capture microdissection, comprising: a solvent; and solute in said solvent, said solute capable of forming a barrier on said biological sample. Another embodiment of the invention is based on a method, comprising: applying a substance to at least a portion of a biological sample that is to undergo laser capture microdissection.

Another embodiment of the invention is based on an apparatus to apply a substance to at least a portion of a biological sample that is to undergo laser capture microdissection, comprising: a container adapted to provide a fluid source of said substance, said container including an orifice that defines a principal plane that is substantially parallel to a primary direction of movement that is to be taken by said biological sample while said substance is being applied. Another embodiment of the invention is based on an apparatus to apply a substance to at least a portion of a biological sample that is to undergo laser capture microdissection, comprising: a dispensing device to deliver or apply a volume of fluid directly onto a biological sample. Delivery or application of the fluid volume to the sample can be in the form of a bead, droplet, spray dispersion, aerosol, spin-coat and/or drip-coat. Another embodiment of the invention is based on an apparatus to apply a substance to at least a portion of a biological sample that is to undergo laser capture microdissection, comprising: a release layer; and a solid layer of said substance coupled to said release layer. Another embodiment of the invention is based on an apparatus to apply a substance to at least a portion of a biological sample that is to undergo laser capture microdissection, comprising: a blade including an indexing surface and a surface to define a gap that defines a principal plane that is held at an acute angle with respect to a perpendicular to a primary direction of movement that is to be taken by said biological sample while said substance is being applied.

These, and other goals and embodiments of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference characters (if they occur in more than one view) designate the same parts. It should be noted that the features illustrated in the drawings are not necessarily drawn to scale.

DESCRIPTION OF PREFERRED EMBODIMENTS

The invention and the various features and advantageous details thereof are explained more fully with reference to the nonlimiting embodiments that are illustrated in the accompanying drawings and detailed in the following description of preferred embodiments. Descriptions of well known components and processing techniques are omitted so as not to unnecessarily obscure the invention in detail.

The purpose of this invention is to provide technology, that is compatible with LCM, to meet some or all of the following needs: prevent non-specific binding of sample to CapSure™; optimal visualization of samples: and stabilization of biological samples. The term "CapSure™" is used herein to generically refer to the combination of an integral portion of an analysis vessel that includes an LCM transfer film and an LCM transfer film carrier. Of course, the invention is not limited to CapSure™.

The invention can include laminating or coating a biological sample (cells or a portion of tissue) mounted on a glass slide or other hard surface material, with a substance. Once the sample is coated, the substance acts to sequester the sample, providing a barrier between the sample and the surrounding environment. The purpose of this barrier is to prevent the sample from making contact with instruments or other items which may be used to manipulate the tissue.

The laminate or coating may be EVA (ethyl vinyl acetate) or some other polymer, modified to have specific properties required to facilitate this invention, or unmodified, and applied in a thickness to be determined. The laminate or coating will be applied to the sample by one of the following methods: dissolving the laminate or coating material supplied in powder, beads or other bulk form, in a solvent; dipping the slide containing the tissue sample into a quantity of the resulting solution; spraying or aerosolizing the laminate or coating solution onto the sample; delivering a volume of the laminate or coating solution onto the surface of the sample. Other application methods may include liquefying the laminate or coating and rolling the slide between rollers (the rollers may be heated and/or cooled); melting a thin sheet of laminate or coating onto the slide using a heat block: and melting a thin sheet of laminate or coating onto the slide with an IR (infrared) sweep. Additional application methods may include spin coating and/or doctor blading, optionally with the below discussed glider device. Also a laminate can be simply pressed onto the tissue without heat.

Application of the laminate or coating to the sample does not interfere with normal handling and processing of the sample, LCM or molecular analysis of the sample. The laminated or coated samples will have the same or better visual appearance as non-coated tissue samples. The laminate or coating will not impede or retard successful LCM transfer of cells or portion of the tissue or prevent access to cells or portions of the tissue for any form of biological analysis.

The invention can include providing a clear coat of polymer on a tissue sample. One embodiment of the invention is based on ELVAX™ 200W diluted in 100% xylene. Xylene is a common histological solvent, known to be compatible with all tissue types and routinely used in tissue preparation for LCM. Rapid xylene evaporation expedites film formation (on evaporation, no polymerization, per se occurs) of the laminate or coating and drying of the sample. The invention can be applied directly to a slide after normal staining or processing. The invention therefore involves only one new step in sample preparation protocol.

The invention (some embodiments of which can be referred to as POLYSLIP™ and/or POLY-SLIP™) was developed as a means of coating the tissue section in order to isolate the surface of the section from the surface of the Capsure™ device. This method of contact surface separation would eliminate the possibility of non-specific material transferring from tissue to Capsure™ devices. Consequently, only tissue targeted for microdissection would be transferred to the Capsure™ device after LCM. This ensures the homogeneity of cell samples collected by LCM and prevents contamination of LCM samples with unwanted macromolecules. During our preliminary testing of the invention, both coated and non-coated tissue sections were microdissected. Pictures of Capsure™ devices used in both procedures are shown in FIGS. 4A–4B, 5A–5C, 6C and 7C. Referring to FIGS. 4A–4B, 5A–5C, 6C and 7C, it is very evident that non-specific material is not present on Capsure™ devices used in laser capture microdissection of inventive coated tissue sections.

The invention can be made from an ethylene vinyl acetate (EVA) polymer, ELVAX™ 200W, diluted with 100% xylene. ELVAX™ 200W is available in pellet or powdered form, which facilitates dissolution in xylene. Since the xylene evaporates rapidly, the invention quickly forms a film and dries on the sample. The invention can be applied directly to tissue sections after staining and processing, as a single additional step in the sample preparation protocol.

We wish to evaluate the feasibility of developing the invention as a product. Our initial feasibility testing program is outlined below.

Initial Product Specifications

1) Performance
   a) Reduction of non-specific transfer by 100% when compared to non-coated tissue sections
   b) Target tissue transfer and recovery efficiency of 100% when compared to transfer and recovery from non-coated sections
   c) Retention of current tissue visualization ability and target capture features (diameter of wetting area; collateral (immediately peripheral to target area) material transfer), relative to non-coated tissue
   d) Demonstration of compatibility with currently used molecular processing methods (PCR, GelElectrophoresis, Molecular Hybridization methods . . . )
   e) Demonstration of stability of the invention for at least 90 days
      i) in xylene solution, sealed in a glass container, at room temperature
   f) Demonstration of stability of tissue sections coated in the invention for at least 90 days
      i) no evidence of tissue degradation, or reduction in macromolecular content or function
      ii) no change in LCM transfer efficiency during that time
2) Application Method
   a) Demonstration tissue sample types
      i) 5 micron paraffin-embedded tissue sections
      ii) Leukocyte enriched blood smears
   b) Application process
      i) Apply even coating
      ii) Air dry 5 minutes
      iii) Perform LCM according to standard procedures
   c) Expected application time—5 minutes (including drying)
   d) Special application equipment requirements—undetermined
   e) Additional LCM instrumentation or equipment modification requirements—none
3) Formulation and Packaging
   a) small volume (25–50 ml.) of fluid in sealed glass container

Technical Feasibility Evaluation Goals

1) Product Design Specifications
   a) Define preliminary formulation
   b) Define preliminary application method
2) Theoretical Performance Report
   a) LCM transfer efficiency (compared to un-coated samples)
   b) Macromolecule (DNA, RNA, Protein) extraction and recovery efficiency (compared to un-coated samples)
   c) Compatibility with current molecular analysis methods (PCR)
   d) Stability of preliminary formulation
   e) Stability of tissue sections coated with the invention (compared to un-coated samples)

Prototypes were made with EVA (i.e., ELVAX™ 200W) dissolved in xylene (i.e., 100% xylene) with and without dye. Operational results with these prototypes are discussed below.

Figure 1A:
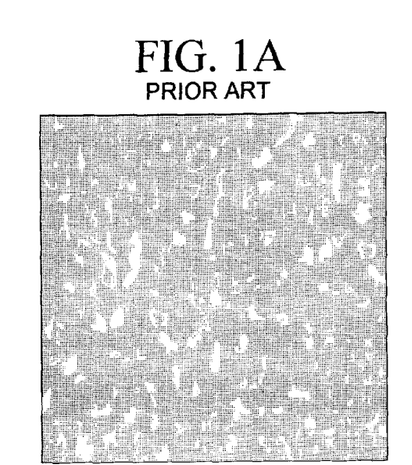
FIGS. 1A–1B illustrate micrographs of control samples that do not have a polymer barrier, appropriately labeled "prior art."
Figure 1B:
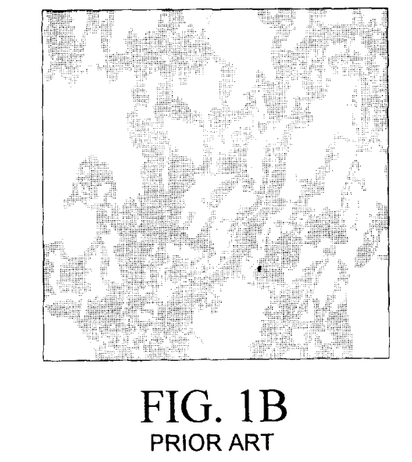
Figure 2A:
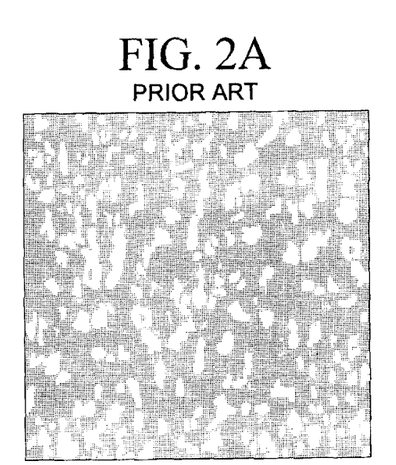
FIGS. 2A–2B illustrate micrographs of samples that do not have a polymer barrier imaged through a diffusing media, appropriately labeled "prior art."
Figure 2B:
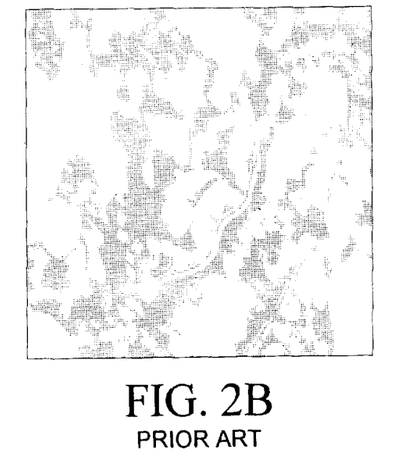
Figure 3A:
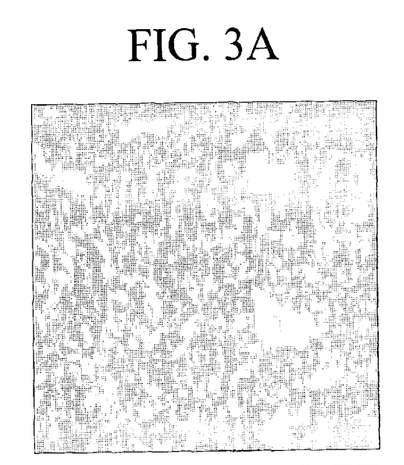
FIGS. 3A–3B illustrate micrographs of samples with a polymer barrier, representing an embodiment of the invention.
Figure 3B:
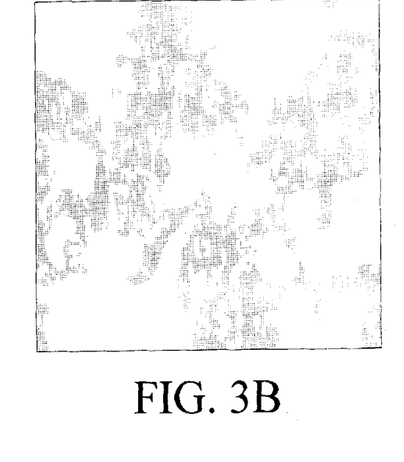

Referring to FIGS. 1A–1B, 2A–2B, and 3A–3B, the visualization advantages of the invention can be appreciated. FIGS. 1A–1B show two views of a sample without a polymer barrier. FIGS. 2A–2B show two views of the sample shown in FIGS. 1A–1B, but imaged through a diffusing media. FIGS. 3A–3B show two views of a sample with a polymer barrier. It can be appreciated that the quality of the visualization shown in FIGS. 3A–3B is surprisingly superior compared to the visualization shown in either FIGS. 1A–1B or FIGS. 2A–2B.

Figure 4A:
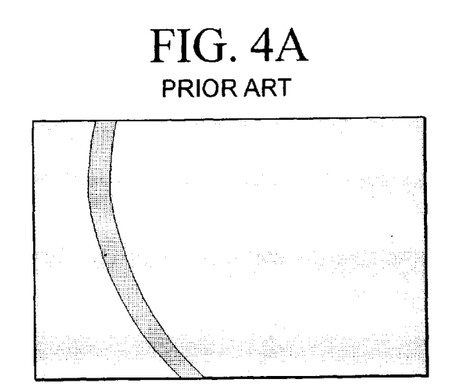
FIGS. 4A–4B illustrate micrographs of CAPSURE devices having on them portions of samples that did not have a polymer barrier prior to acquisition by LCM, appropriately labeled "prior art."
Figure 4B:
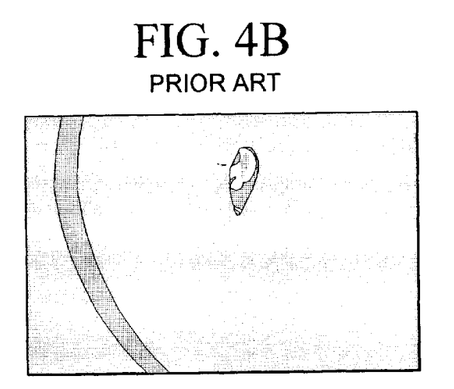
Figure 5A:
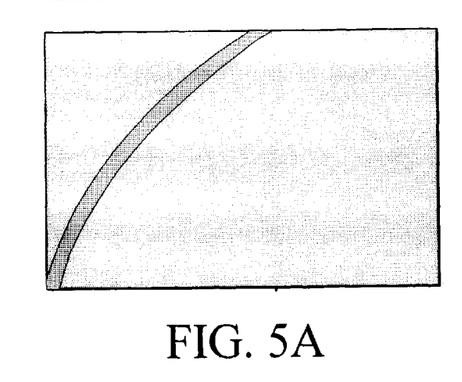
FIGS. 5A–5C illustrate micrographs of CAPSURE devices having on them portions of samples that had a polymer barrier prior to acquisition by LCM, representing an embodiment of the invention.
Figure 5B:
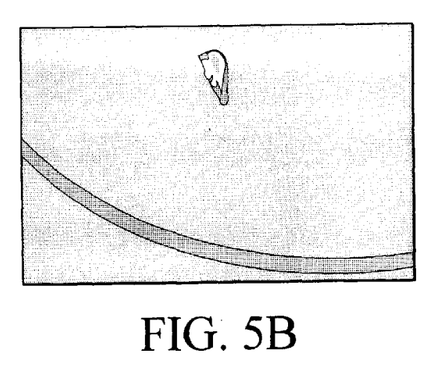
Figure 5C:
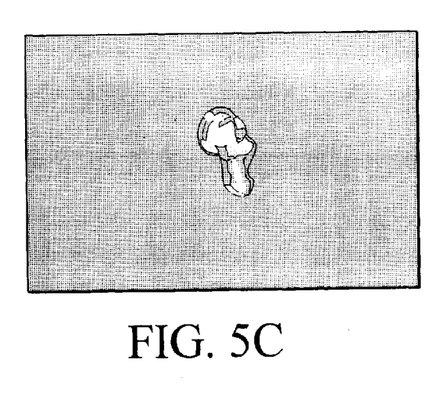

Referring to FIGS. 4A–4B and 5A–5C, the non-specific transfer advantages of the invention can be appreciated. FIGS. 4A–4B show images of an LCM transfer film (seen through an LCM transfer film carrier) both before LCM acquisition of a sample portion from a sample that did not have a polymer barrier (FIG. 4A) and after (FIG. 4B). FIGS. 5A–5B show an images of an LCM transfer film (seen through an LCM transfer film carrier) both before LCM acquisition of a sample portion from a sample that had a polymer barrier (FIG. 5A) and after (FIG. 5B). FIG. 5C shows a close-up of the sample portion shown in FIG. 5B. The substantial absence of non-specific transfer with the use of the invention is clearly evident.

Figure 6A:
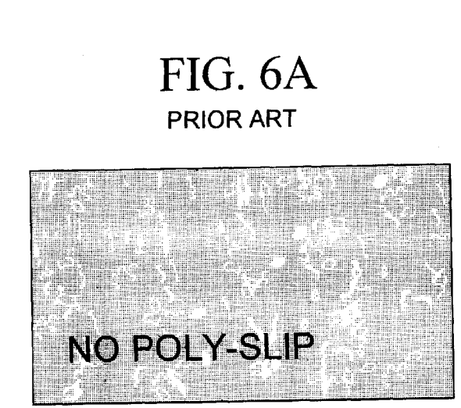
FIGS. 6A–6B illustrate micrographs of samples that did not have a polymer barrier prior to acquisition by LCM, appropriately labeled "prior art."
Figure 6B:
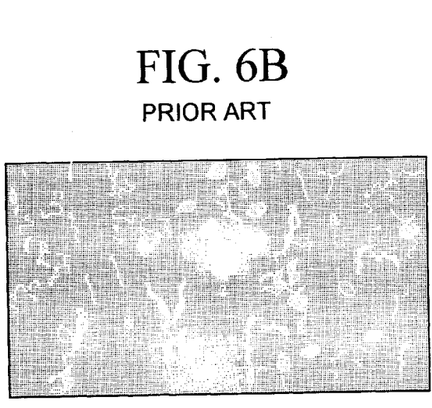
Figure 6C:
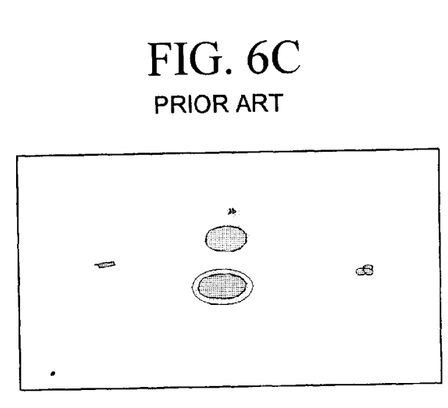
FIG. 6C illustrates a micrograph a CAPSURE device having on it a portion of a sample that did not have a polymer barrier prior to acquisition by LCM, appropriately labeled "prior art."
Figure 7A:
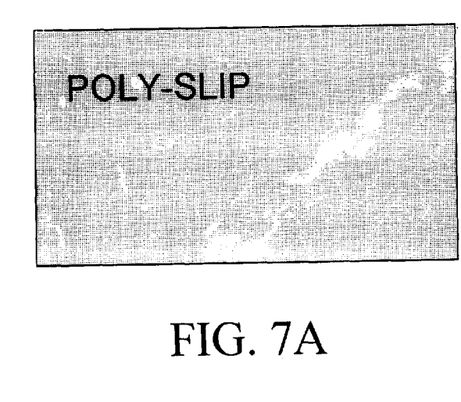
FIGS. 7A–7B illustrate micrographs of samples and portion thereof that had a polymer barrier prior to acquisition by LCM, representing an embodiment of the invention.
Figure 7B:
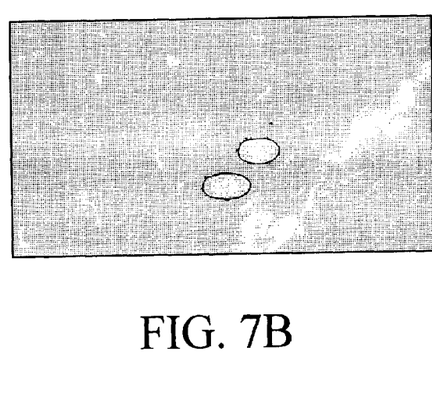
Figure 7C:
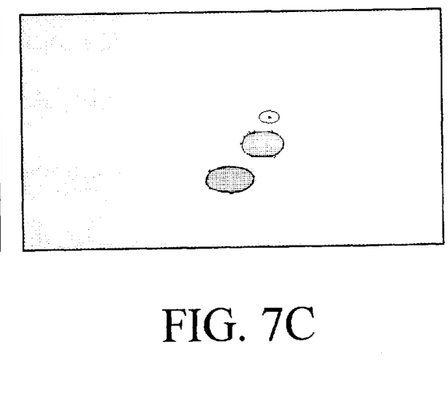
FIG. 7C illustrates a micrograph of a CAPSURE device having on it a portion of a sample that had a polymer barrier prior to acquisition by LCM, representing an embodiment of the invention.

Referring to FIGS. 6A–6C and 7A–7C, both the visualization and non-specific transfer advantages of the invention can be appreciated. FIGS. 6A–6C show visualizing before LCM, visualizing after LCM, and the resulting transferred portion of a sample that did not have a barrier, respectively. In contrast, FIGS. 7A–7C show visualizing before LCM, visualizing after LCM, and the resulting transferred portion of a sample that had a barrier, respectively. It can be appreciated that visualizing is significantly improved and non-specific transfer is significantly reduced as a result of the barrier. Currently, when Capsure™ devices make contact with a tissue section during Laser Capture Microdissection (LCM), the total working area of the Capsure™ device touches the surface of the tissue section. Due to the friable nature of tissue sections, loose material (whole cell or macromolecular) is likely to adhere to the Capsure™ device during LCM. This is known as non-specific transfer. Since LCM sample recovery involves extraction of the material on the surface of a Capsure™ device, any non-specific material present can cause sample contamination.

The invention was developed as a means of coating the tissue section in order to isolate the surface of the section from the surface of the Capsure™ device. This method of contact surface separation would eliminate the possibility of non-specific material transferring from tissue to Capsure™ devices. Consequently, only tissue targeted for microdissection would be transferred to the Capsure™ device after LCM. This ensures the homogeneity of cell samples collected by LCM and prevents contamination of LCM samples with unwanted macromolecules.

Applying the substance to a tissue section prior to LCM merely requires applicators and application methods that are compatible with current tissue preparation methods. Extracting substance coated material from the Capsure™ device surface is compatible with extraction methods, and buffers, and can be used under the various temperature requirements normally part of molecular analysis protocols.

Substance Formulations Tested

Table 1 lists some formulations that have been used in different experiments to demonstrate their ability to abate non-specific transfer and still permit microdissection of tissue sections.

TABLE 1

Compositions

| POLYMER | SOLVENT | % | NS detected on sample |
|---|---|---|---|
| Elvax 200W | Cyclohexane | .9 | None |
| Elvax 200W | Cyclohexane/Ether 30/70 | .2 | Low |
| Elvax 200W | Cyclohexane/Ether 30/70 | .6 | None |
| Elvax 200W | Cyclohexane/Ether 30/70 | .9 | None |
| Elvax 200W | Cyclohexane/Pentane 30/70 | .9 | None |
| Elvax 200W | Xylene | .9 | None |
| Elvax 200W | Xylene | 1 | None |
| Elvax 200W | Xylene | 2.5 | Low |
| Elvax 200W | Xylene | 5 | None |
| Elvax 200W | Xylene | 7.5 | None |
| Elvax 200W | Xylene | 10 | None |
| Elvax 450 | Cyclohexane | 1 | None |
| Elvax 450 | Xylene | 1 | None |
| Paraffin Mp. 56° C. | Xylene | 1 | Low |
| Paraplast ™ | Cyclohexane | 1 | Low |
| Poly α-metyl styrene | Xylene | 1 | None |
| Polyester Wax Mp. 37° C. | Xylene | 1 | Low |

The following section is descriptive generally for either liquid or solid embodiments of the invention. In most cases a polymeric material is desirable, but in some cases the materials are not polymers. For example, paraffin and polyester waxes are useful, but do not fall into the class of materials commonly referred to as polymers.

In addition to using a solid film and coating from solution, one could use a system which undergoes curing. The curing could be from monomers, or could involve crosslinking of a polymeric solution. If the curing is done from monomers, it would be possible to have a solvent free liquid system. Examples of curable systems can be acrylic, urethane, or epoxy chemistry.

The materials for use in the invention must be optically transparent, and should have little to no color. In order to use them in the liquid application method, they must be soluble or dispersible in the solvent used. It is desirable that they be film-forming materials, but that is not an absolute requirement. The film of material must have a cohesive strength which is less than the tissue so that only the tissue in contact with the selected tissue portion is transferred. In some cases it is useful for the inventive materials to undergo softening when heated.

The following materials are suitable for use with the invention:

Waxes or low molecular weight oligomers—Paraffin, Polyester, Wax

Polyethylene—especially low molecular weight

Ethylene co-polymers such as poly (ethylene-co-vinyl acetate) (EVA), and poly(ethylene-co-acrylic acid) (EAA).

Acrylates, urethanes, epoxies

Water borne polymers and oligomers—such as Polyvinyl alcohol (PVA), Polyvinyl Pyrolidone (PVP), Polyethylene oxide (PEO), Polyethylene glycol (PEG), and Poly acrylic acid.

Polyisobutylene

Methods of Application

Figure 9:
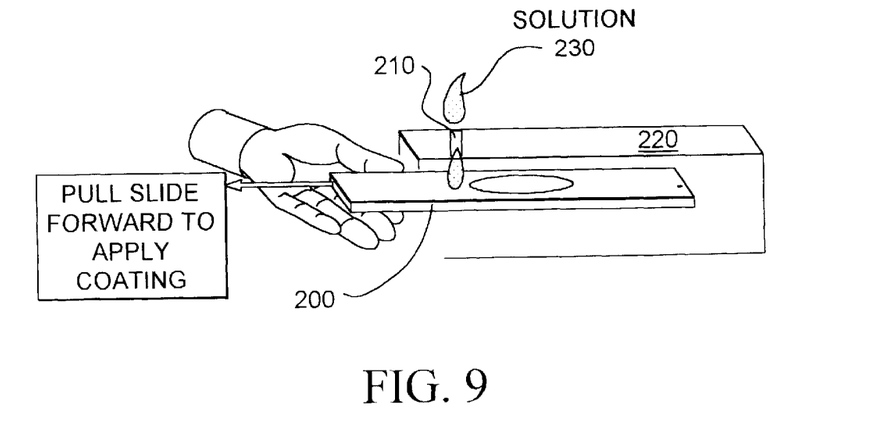
FIG. 9 illustrates a schematic perspective view of a method of processing a biological sample, representing an embodiment of the invention.

1) Referring to FIG. 9, an apparatus for applying the inventive composition to a glass slide mounted biological sample is depicted. A slide 200 is pulled along underneath an orifice 210 in a container 220 through which a barrier forming solution 230 flows.

Figure 11A:
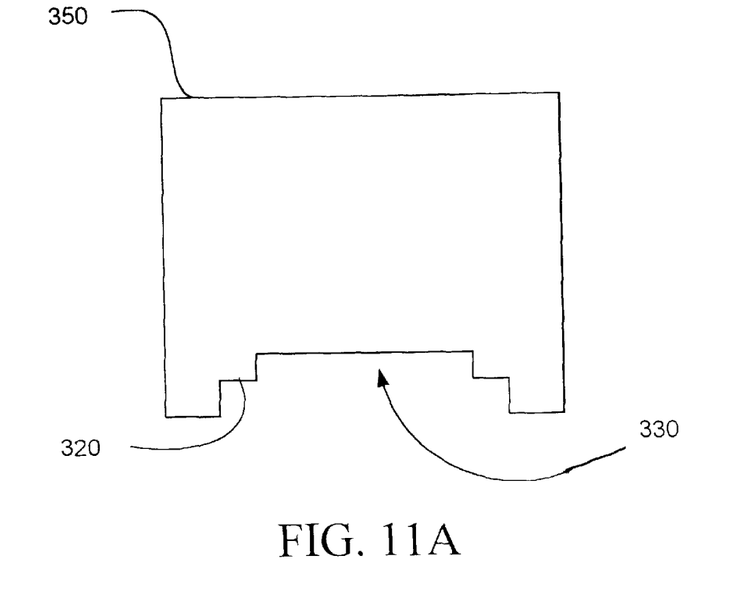
FIGS. 11A–11B illustrate schematic views of a coating process, representing an embodiment of the invention.
Figure 11B:
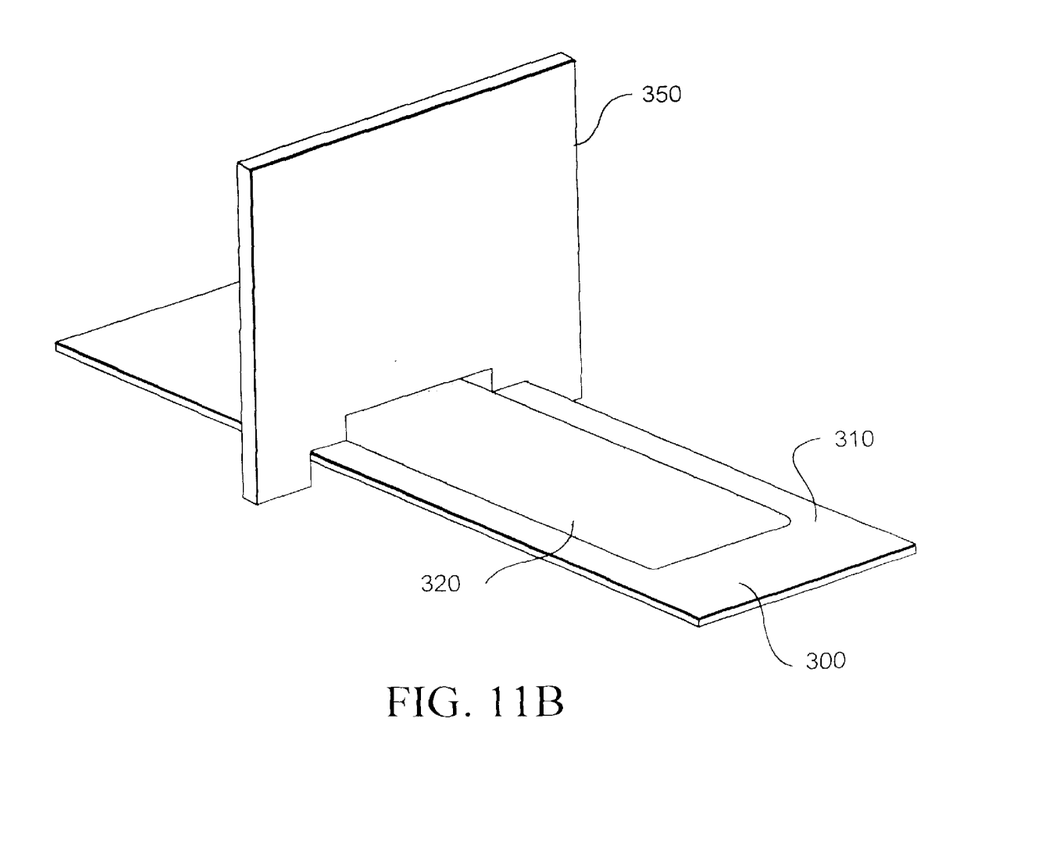

2) Referring to FIGS. 11A–11B, one method of application which is a subset of the invention is a device 350 which fits over a microscope slide 300, indexes off of a surface 310, and creates a fixed gap which spreads the fluid evenly when pulled across the surface of the slide. The device 350 includes a first recess 320 that indexes on the surface 310. The device 350 also includes a second recess 330 that sets a gap for spreading the coating 320. An operator can slide the device 350 across the slide 300 to form an even coat of substance. This device can be referred to as a glider.

An experiment will now be described. The objective of this experiment was to test the level of Non-Specific abatement provided by the inventive formulation 5% ELVAX™ 200W in xylene (5% 200W).

Two Hematoxylin/Eosin(H&E)-stained brain tissue sections from the same lot were selected for this experiment. One was coated with a thin layer of 5% 200W. An uncoated H&E-stained brain section was used as a control. Target cells (500, 250, 100, 50, 10 and 5 per section) were Laser Capture Microdissected (LCM) from each section. One blank Capsure™ device was included as a control for each sample set.

Cellular material was extracted using a Proteinase K-based extraction protocol. Extracted material was treated with PicoGreen® fluorescent DNA Quantitation solution and then quantitated on a Packard Fluorcount® Fluorimeter.

Total fluorescence for samples and controls was measured on the Fluorcount® Fluorimeter and recorded. Background fluorescence in the system was established by measuring the total fluorescence of a volume of the Proteinase K extraction buffer equivalent to that of each sample and control.

Figure 8:
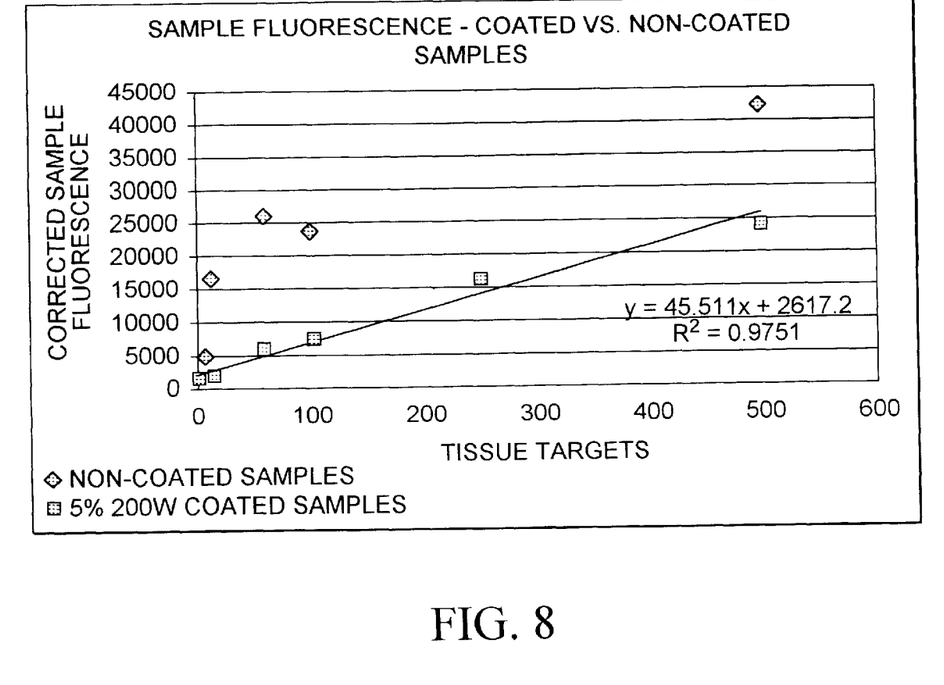
FIG. 8 compares fluorescence as a function of the number of tissue targets between non-coated samples and 5% 200W coated samples, representing an embodiment of the invention.

As shown in Table 2 and FIG. 8, non-coated tissue samples gave variable fluorescence readings, with no apparent correlation between the number of cells in the sample and sample fluorescence. On the other hand, 5% 200W coated tissue samples showed a reasonably linear relationship ($r^2=0.9751$) between the number of targets and both total and corrected sample fluorescence. Coated samples also had an overall lower fluorescence level than non-coated samples.

It is reasonable to conclude that the presence of non-specific material could account for both the variability of fluorescence in the non-coated tissue samples, as well as the increased fluorescence, when compared to coated tissue samples.

TABLE 2

Sample Fluorescence
Coated vs. Uncoated Samples

|  |  | TARGETS → | | | | | | |
| --- | --- | --- | --- | --- | --- | --- | --- | --- |
|  |  | 500 | 250 | 100 | 50 | 10 | 5 | Blank |
| Non-Coated Tissue | TSF | 44531 | 18437 | 26166 | 27125 | 19882 | 6657 | 3852 |
|  | CSF | 42645 | 16551 | 24281 | 25238 | 17106 | 4770 | 1965 |
| 5% 200W Coated Tissue | TSF | 25866 | 18507 | 9276 | 7349 | 4010 | 4478 | 3680 |
|  | CSF | 23980 | 16621 | 7389 | 5463 | 2124 | 2592 | 1794 |

LEGEND - TSF - Total Sample Fluorescence; CSF - Corrected Sample Fluorescence (Digestion Buffer Blank TF was subtracted from Sample TF)

Another experiment will now be described. The objective of this experiment was to test the level of non-specific abatement provided by the inventive composition of ELVAX™ 200W in xylene (5% 200W).

Unstained human brain sections were used for this experiment. Sections were coated with 5% 200W. Control sections were uncoated. Laser capture microdissection (LCM) was done in highly nucleated areas of the section, with each target acquiring between 1 and 2 nuclei per shot, as well as matrix material. 50 LCM targets were captured in each sample and 10 samples were taken from both the coated and non-coated sections Samples were extracted with a Proteinase K extraction buffer. The extracted samples were treated with PICOGREEN™ Fluorescent DNA Quantitation solution and then quantitated on a Molecular Dynamics FLUORIMAGER™.

Fluorescent readings were taken for each sample and the median pixel fluorescence (MPF) for each sample was recorded. Background fluorescence in the system was established by measuring the total fluorescence of a volume of the Proteinase K extraction buffer equivalent to that of each sample and control. A corrected MPF (cMPF) was determined by subtracting the background fluorescence from the MPF of each sample and control.

The fluorescence data is shown in Table 3. The average cMPF value for 10 samples from uncoated sections was 15.75 (s.d. 9.58). The average mPF value for 10 5% 200W samples was 3.30 (s.d. 0.67). The high variability of sample fluorescence in the uncoated sections, as compared to coated sections, would seem to indicate the presence of non-specific material in the sample.

TABLE 3

Fluorescent Readings

| Sample # | Uncoated Section Control cMPF | 5% 200W Coated Section Sample cMPF |
| --- | --- | --- |
| 1 | 6.46 | 3.54 |
| 2 | 4.16 | 2.87 |
| 3 | 27.52 | 3.34 |
| 4 | 8.50 | 3.42 |
| 5 | 7.65 | 3.54 |
| 6 | 12.46 | 3.30 |
| 7 | 19.31 | 3.06 |
| 8 | 15.46 | 2.91 |
| 9 | 31.57 | 4.84 |
| 10 | 24.45 | 2.22 |
| Mean | 15.75 ± 9.59 | 3.30 ± 0.67 |

An experiment will now be described. The following materials were used:

slides with blood-smear tissue samples;

blank slides with no tissue sample for polymer coating only;

polymer solutions: paraffin wax with cyclohexane solvent;

Slide glider of clearance of 0.015" and width 25.4", and slide spinner with slide holder, both were used for spreading polymer solutions.

Regular Capsure™ devices and 4 um rail Capsure™ devices were experimented with. Life savers are adhesive acrylic "doughnuts" which adhere to the bottom of the Capsure™ device and define an extraction volume of 10 microliters (well diameter=0.125 in . . . The objective of this experiment was to test the level of Non-Specific abatement provided by the inventive formulations described in the next paragraph.

Two sets of polymer solutions with cyclohexane solvent at concentration of 2.5% (g wt. polymer by ml volume solvent), and the other set included each polymer mixed with Cyclohexane at 5% concentration. 2.5% solutions were prepared by mixing 0.25 g of polymer with 10 ml of solvent, and similarly 5% solutions were made by mixing 0.50 g of polymer with 10 ml of solvent. Polymers normally dissolved after placing bottled solutions in water bath at 32.5° C. for 10–15 minutes. Four solutions in all were made based on two polymers and two concentrations.

Coated each of the polymer solutions at 2.5% concentration on three blood tissue slides, using the glider method. When applying with glider, 30 uL volume of polymer solution was pipetted just in front of the tissue and immediately spread with the glider held at 30° angle with respect to the perpendicular and drawn quickly over the slide. Also coated each of the 5% polymer solutions on one blood tissue slide, using the slide spinner. When using spinner method, 40 uL volume of polymer solution was placed in the slide holder so that 20 uL went in each hole at top of holder. Each slide was spun at high speed and time settings (DD settings).

Eight slides in all were coated, 6 using each of the 2.5% polymer solution applied with the glider (3 slides with Paraffin and 3 with Polyester-Wax), and 2 using each of the 5% polymer solution applied with the spinner (1 with Paraffin and 1 with Polyester-Wax). The similar coated slides were used for different Capsure™ device types (regular and rail) and different extraction methods (with or no life savers). Please see experiment outline for clarification.

Applied each of the 2.5% and the 5% polymer solutions on a blank slides (4 slides all together) with no tissue sample on slide. This is done to test for any fluorescence contribution from the polymer coating.

After polymer solution application, every slide was left under the hood for 45 min to dry then placed in desiccator for 4 hours before performing LCM. The thickness of the polymer layer is estimated at 4–6 um or less.

For each polymer coated slide, 4 Capsure™ devices were used. For sets using regular Capsure™ devices and no life saver extraction method, LCM was performed at 5 locations, one in the middle and the others around, half way between middle point and edge. In each location, 15 shots were fired, totaling to 75 shots per Capsure™ device. For sets using rail Capsure™ devices and regular Capsure™ devices with life saver extraction method, 75 shots were fired at center of Capsure™ device. Acquisition was performed using a commercial LCM instrument at setting of 0.8–1.0 ms duration and 50–80 mW power, with multiple firing (2–3 times). An LCM instrument was used to confirm the number of successful shots and verify extraction in post stained Capsure™ devices.

Extraction was performed on the paraffin coated blank slides and paraffin coated blood smear slides, using regular and rail Capsure™ devices, with or without life savers. These samples had reasonable shot capture efficiency and low non specific cell count. At a later time, PCR was performed on 2.5% Paraffin coated blood smear samples. PCR was successful.

The results summarized in Table 4 below show good tissue transfer, low levels of non-specific cells, and effective extraction of DNA from cells.

Blank paraffin coated slides (2.5 and 5%) were also extracted, and pico green analysis and visual inspection indicated no fluorescence contribution from polymer.

To verify extraction, the Capsure™ devices are restained and examined with an LCM instrument to visually determine extraction efficiency. Apparently most Capsure™ devices were left in heating block during extraction too long which resulted in melting of Capsure™ devices' surfaces. Only five Capsure™ devices were not damaged and verification was performed on them, showing that extraction occurred 100%.

TABLE 4

LCM Results for Blank and Blood Smear Slides Coated with Paraffin in Cyclohexane Solutions

| Sample | Cap # | Shots attempted | Shots capture eff. % | Estimated cells captured (visual) | Estimated Non-specific cells (visual) | Extraction eff. % (visual) |
|---|---|---|---|---|---|---|
| Blank (no tissue) with 2.5% soln Paraffin with glider | 1B* | 75 | | | 0 | (not performed) |
| | 2B | 75 | | | 0 | |
| | 3B | 75 | | | 0 | |
| | 4B | 75 | | | 0 | |
| | total | 300 | | | 0 | |
| 2.5% Paraffin with glider regular caps no life saver | 1B | 75 | 45% | 42 | 4 | *** |
| | 2B | 75 | 92% | 89 | 100 | 100% |
| | 3B | 75 | 80% | 76 | 0 | *** |
| | 4B | 75 | 92% | 96 | 6 | 100% |
| | total | 300 | 78% | 303 | 110 | ■■■■■■■■■■ |
| 2.5% Paraffin with glider regular caps with life saver | 1B | 75 | 11% | 8 | 0 | *** |
| | 2B | 75 | 89% | 79 | 1 | *** |
| | 3B | 75 | 92% | 76 | 0 | *** |
| | 4B | 75 | 97% | 92 | 0 | *** |
| | total | 300 | 72% | 255 | 1 | |
| 2.5% Paraffin with glider rail caps with life saver | 1R* | 75 | 95% | 79 | 0 | *** |
| | 2R | 75 | 89% | 93 | 0 | 100% |
| | 3R | 75 | 100% | 87 | 0 | *** |
| | 4R | 75 | 97% | 100 | 0 | 100% |
| | total | 300 | 95% | 359 | 0 | |
| 5% Paraffin with spinner regular caps no life saver | 1B | 75 | 63% | 52 | 6 | *** |
| | 2B | 75 | 88% | 74 | 22 | 100% |
| | 3B | 75 | 81% | 78 | 11 | *** |
| | 4B | 75 | 79% | 69 | 11 | *** |
| | total | 300 | 78% | 273 | 50 | *** |

*B = caps manufactured with automated method. and R = rail caps of 4 um height
***These caps' surfaces were deformed due to staying in heat block too long during extraction Another example will now be described. The following materials were used:

Tissue Samples: Nine blood-smear tissue samples were used, one for control (no invention), and eight for inventive polymer coating.

Polymer Solutions: Paraffin and Polyester Wax polymers were used along with Cyclohexane and xylene solvents.

Slide glider of clearance of 0.015" and slide spinner, both were used for spreading polymer solution.

Capsure™ devices made from new manufacturing method (type B) were used. Capsure™ devices came from lots #99K15B and #99L16B.

Two sets of polymer solutions were prepared, one set included each polymer mentioned above mixed with Cyclohexane, and the other set included each polymer mixed with xylene solvent. Each polymer solution was prepared by mixing 0.5 g polymer to 20 ml of solvent (2.5% wt. by volume solutions). Polymers normally dissolved after placing bottled solutions in water bath at 32.5° C. for 10–15 minutes. Four solutions in all were made based on two polymers and two solvents.

Coated each of the polymer solutions on two blood tissue slides, using the glider method on one slide and the spinner method on the other. For the glider method, 30 uL volume of polymer solution was pipetted just in front of the tissue and immediately spread with the 0.015" glider held at 30° angle with respect to the perpendicular. For the spinner method, 40 uL volume of polymer solution was placed in the slide holder so that 20 uL went in each hole at top of holder. Each slide was spun at medium speed and time (cc settings). Eight slides in all were coated, 4 using each of the polymer solution applied with the glider, and 4 using each of the polymer solution applied with the spinner.

After polymer solution application, every slide was left under the hood for 4 hours to dry then placed in desiccator overnight before performing LCM. The thickness of the polymer layer is estimated at 4–6 um or less.

For the control and each polymer coated slide, 4 Capsure™ devices were used. For each Capsure™ device LCM was performed at 5 locations, one in the middle and the others around, half way between middle point and edge. In each location, 15 shots were fired (except for control's two first Capsure™ devices at 10 shots/location) at LCM instrument setting of 1–1.2 ms duration and 52–65 mW power.

Each Capsure™ device then should have 75 shots total attempted. Fluorescence light was not available when firing shots. However, an LCM with fluorescence Capsure™ deviceability was used to confirm number of successful shots afterwards.

Extraction was performed on the control and only half of the coated tissue samples due to low shot capture efficiency and/or high non-specific count on some sample Capsure™ devices. Extraction was not performed on the later samples.

The results of this example are summarized in Tables 5 and 6. Capturing efficiency was high for control samples (no inventive coating) as well as Paraffin in Cyclohexane ones (using glider) as indicated in Table 4 Non-specific count was high in control Capsure™ devices (100–500) while it dropped dramatically for samples mentioned above (0–131).

Extraction on control and selected inventive samples was successful 100% based on visual inspection (restaining Capsure™ devices post extraction). Quantification of cells captured, however, is difficult to estimate from the picogreen analysis, but evident of extraction is apparent and the trend is established.

TABLE 5

LCM Results for Control and Polymer/Cyclohexane Samples

| Sample | Cap # | Shots attempted | Shots capture eff. % | Estimated cells captured (visual) | Estimated Non-specific cells (visual) | Extraction eff. % (visual) |
|---|---|---|---|---|---|---|
| Control | 1B* | 50 | 100% | 70 | >150 | (not performed) |
| (no polyslip coating) | 2B | 50 | 100% | 80 | 100 | |
| | 3B | 75 | 99% | 128 | >500 | |
| | 4B | 75 | 99% | 121 | >500 | |
| | total | 250 | 99% | 399 | >1250 | |
| Polyester-Wax in | 1B | 75 | 27% | 22 | 0 | 100% |
| Cyclohexane with glider | 2B | 75 | 13% | 10 | 0 | 100% |
| | 3B | 75 | 28% | 24 | 0 | 100% |
| | 4B | 75 | 40% | 34 | 0 | 100% |
| | total | 300 | 27% | 90 | 0 | 100% |
| Paraffin in | 1B | 75 | 77% | 79 | 52 | 100% |
| Cyclohexane with glider | 2B | 75 | 75% | 65 | 22 | 100% |
| | 3B | 75 | 88% | 84 | 10 | 100% |
| | 4B | 75 | 79% | 71 | 31 | 100% |
| | total | 300 | 80% | 299 | 115 | 100% |
| Polyester-Wax in | 1B | 75 | 37% | 32 | 45 | (not performed) |
| Cyclohexane with spinner | 2B | 75 | 47% | 38 | 45 | |
| | 3B | 75 | 21% | 18 | 39 | |
| | 4B | 75 | 16% | 12 | 95 | |
| | total | 300 | 30% | 100 | 224 | |
| Paraffin in | 1B | 75 | 71% | 69 | 30 | (not performed) |
| Cyclohexane with spinner | 2B | 75 | 87% | 75 | 100 | |
| | 3B | 75 | 85% | 80 | 100 | |
| | 48 | 75 | 88% | 84 | 100 | |
| | total | 300 | 83% | 308 | 330 | |

*B = caps manufactured with automated method
***These caps were not extracted due to low shot capt. eff. % and/or high non-specific cells

TABLE 6

LCM Results for Polymer/Xylene Samples

| Sample | Cap # | Shots attempted | Shots capture eff. % | Estimated cells captured (visual) | Estimated Non-specific cells (visual) | Extraction eff. % (visual) |
|---|---|---|---|---|---|---|
| Polyester-Wax in | 1B* | 75 | 43% | 39 | 0 | 100% |
| Xylene with glider | 2B | 75 | 71% | 57 | 30 | 100% |
| | 3B | 75 | 56% | 51 | 15 | 100% |
| | 4B | 75 | 47% | 49 | 20 | 100% |
| | total | 300 | 54% | 196 | 65 | 100% |
| Paraffin in | 1B | 75 | 19% | 15 | 100 | (not performed) |
| Xylene with glider | 2B | 75 | 0% | 0 | 4 | |
| | 3B | 75 | 19% | 19 | 30 | |
| | 48 | 75 | 0% | 0 | 0 | |
| | total | 300 | 9% | 34 | 134 | |
| Polyester-Wax in | 1B | 75 | 40% | 35 | 70 | 100% |
| Xylene with spinner | 2B | 75 | 72% | 58 | 25 | 100% |
| | 3B | 75 | 80% | 73 | 2 | 100% |
| | 4B | 75 | 81% | 67 | 40 | 100% |
| | total | 300 | 68% | 233 | 137 | 100% |
| Paraffin in | 1B | 75 | 59% | 51 | 300 | (not performed) |
| Xylene with spinner | 2B | 75 | 52% | 55 | 200 | |
| | 3B | 75 | 63% | 58 | 500 | |
| | 4B | 75 | 47% | 40 | 200 | |
| | total | 300 | 55% | 204 | 1200 | |

*B = caps manufactured with automated method
***These caps were not extracted due to low shot capt. eff. % and/or high non-specific cells

Non Specific Barrier Film

Another embodiment of the invention will now be described. The purpose of this invention is to prevent contaminating material from migrating from the surface of the tissue slide to the Capsure™ device EVA film.

This embodiment includes a thin layer of transfer adhesive (substance) constructed on a release liner. The transfer adhesive can be extruded or solvent coated on to a liner which has its surface adherence controlled to effect a 'release'. The thickness of the substance can be controlled by line speed on a web, the temperature of a chill roll and the screw speed of an extruder, if an extrusion process used. If a knife-over coater process is used, then coat weight and percentage solids loading concentration in the solvent, in conjunction with line speed and coat roll depth can be utilized to keep the thickness of the substance within specification.

The substance which is to form the barrier layer should be chosen to be a compatible polymer, or polymer blend, to mix with the hot melt adhesive (transfer film) used in LCM. An example of this is ELVAX™ 200W, which is an ethyl vinyl acetate (EVA). Other choices would be blends of EVAs, and/or alloys of EVA and LDPE or wax. The melt index and melt temperature would be chosen to interact in a complimentary way with the LCM process.

Figure 10A:
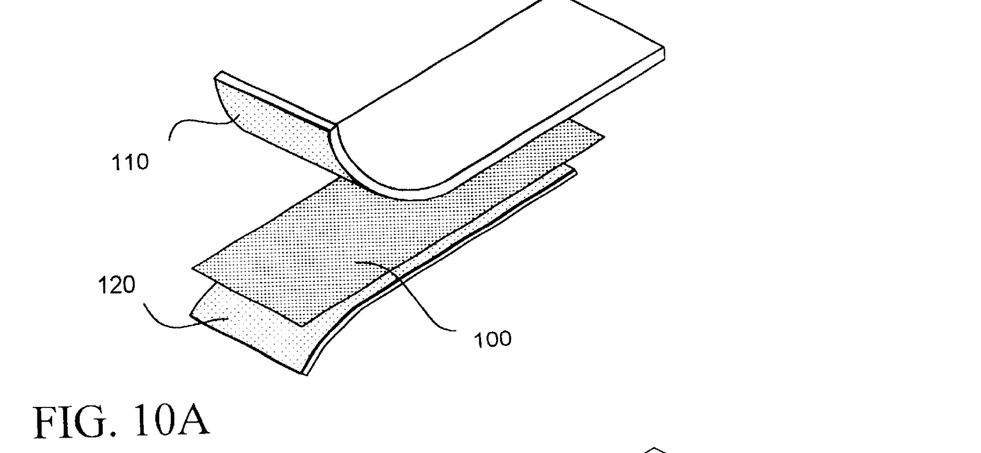
FIGS. 10A–10C illustrate schematic perspective views of a lamination process, representing an embodiment of the invention.
Figure 10B:
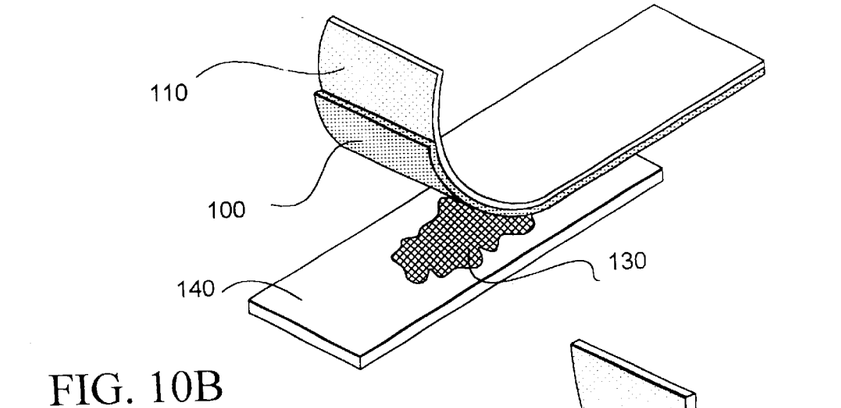
Figure 10C:
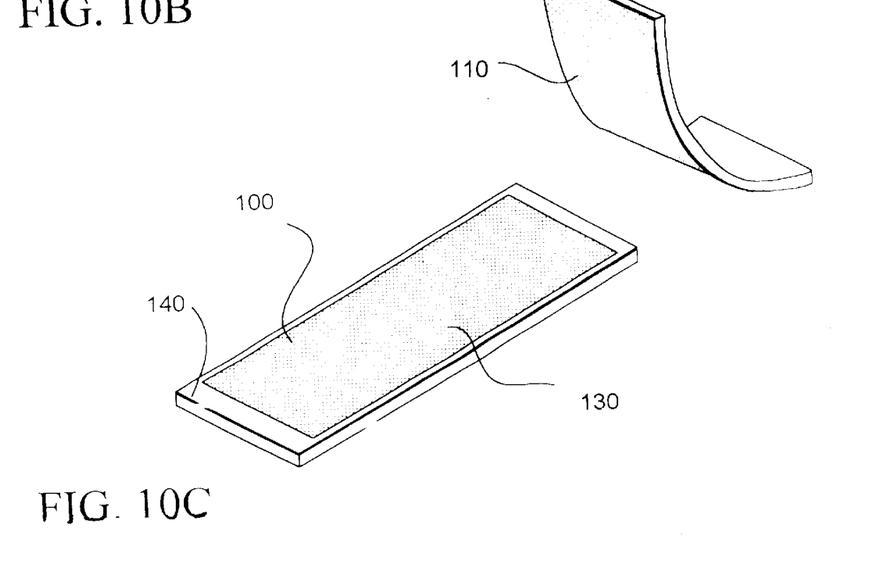

Referring to FIGS. 10A–10C, a film 100 is made sandwiched between two layers 110, 120 of release liner (e.g., Polyester). In use, one of the layers (e.g., 120 ) is peeled back and discarded and the upper layer 110 with the film 100 (aka substance, barrier, transfer adhesive) is layered on top of a tissue section 130 located on a microscope slide 140. Gentle pressure and/or heat is then applied to preferentially adhere the film 100 to the tissue 130 and glass 140. The assembly is allowed to cool and the upper liner 110 is then peeled back and discarded. The tissue sample 130 on the slide has been effectively covered with a transfer adhesive barrier layer and is now ready for LCM. In this way, the tissue 130 has been protected from touching the surface of the LCM transfer device (transfer film) by the presence of the barrier film. The invention reduces non-specific transfer. Hence, no contamination from non-specifically bound tissue is possible. The LCM process is unaffected by the barrier because it miscibly interacts with the transfer film. The barrier goes with the acquired portion of the tissue and the Capsure™ device after the micro-dissection has been performed.

The context of the invention includes laser capture microdissection. The context of the invention also includes handling, purification and/or analysis of biological material obtained via laser capture microdissection.

The invention can also be included in a kit. The kit can include some, or all, of the components that compose the invention. More specifically, the kit can include the ingredients that compose the composition, a container to hold the composition and/or ingredients, and other components of the invention such as dye(s) and/or applicator(s). The kit can also contain instructions for practicing the invention and apparatus for carrying out the invention. Unless otherwise specified, the components (and apparatus and/or instructions) of the kit can be the same as those used in the invention.

The below-referenced U.S. Patent and U.S. Patent Applications disclose embodiments that were satisfactory for the purposes for which they were intended. The entire contents of U.S. Pat. No. 5,985,085 are hereby expressly incorporated by reference into the present application as if fully set forth herein. The entire contents of U.S. Ser. Nos. 08/800,882; 09/018,452: 09/121,691; 09/121,635; 09/058,711; 09/121,677; 09/208,604; 09/538,862; 09/344,612; 08/984,979; and 09/357,423 are hereby expressly incorporated by reference into the present application as if fully set forth herein.

The term approximately, as used herein, is defined as at least close to a given value (e.g., preferably within 10% of, more preferably within 1% of, and most preferably within 0.1% of). The term substantially, as used herein, is defined as at least approaching a given state (e.g., preferably within 10% of, more preferably within 1% of, and most preferably within 0.1% of). The term coupled, as used herein, is defined as connected, although not necessarily directly, and not necessarily mechanically.

While not being limited to any particular performance indicator, preferred embodiments of the invention can be identified one at a time by testing for improved visualization. The test for the presence of improved visualization can be carried out without undue experimentation by the use of a simple and conventional optical microscope experiment. The apparent contrast of detail within the samples can be characterized, both with and without dyes. Another way to seek preferred embodiments one at a time is to test for reduced non-specific pick-up. The test for reduced non-specific pick-up can be carried out without undue experimentation by the use of a post LCM inspection of the size and shape of the portion of the sample that remains adhered to the LCM transfer film. The amount of sample still adhered to the LCM transfer film beyond the spot diameter can be measured (with optional variation of power density), with special attention being given to asymmetric non-specific transfers as undesirable. Another way to seek preferred embodiments one at a time is to test for reduced sample degradation (with optional variation of storage times before LCM). The test for reduced sample degradation can be carried out without undue experimentation by testing the accuracy of diagnostic assays on LCM acquired portions of samples that are known to be positive.

All the disclosed embodiments of the invention described herein can be realized and practiced without undue experimentation. Although the best mode of carrying out the invention contemplated by the inventors is disclosed above, practice of the invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the barrierized samples described herein can be physically separate modules, it will be manifest that the barrierized samples may be integrated into additional apparatus with which they are associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements.

The appended claims are not to be interpreted as including means-plus-function limitations, unless such a limitation is explicitly recited in a given claim using the phrase "means for." Expedient embodiments of the invention are differentiated by the appended subclaims.

What is claimed is:

1. A method of processing a sample for laser capture microdissection, comprising:

providing a sample;

mounting the sample on a surface;

providing a transfer film;

providing a barrier layer adapted to substantially eliminate non-specific transfer of the sample to the transfer film;

applying the barrier layer over the sample;

placing the transfer film in juxtaposition to the sample;

activating the transfer film; and transferring a portion of the sample to the transfer film.

2. The method of claim 1, wherein said substance is provided as a liquid and applying said substance includes coating said liquid on said biological sample.

3. The method of claim 2, wherein coating includes at least one technique selected from the group consisting of spraying, dipping and dripping.

4. The method of claim 2, wherein coating includes at least one technique selected from the group consisting of rolling and spin coating.

5. The method of claim 1, wherein the barrier layer is provided as a film and applying said substance includes laminating said film to the sample.

6. The method of claim 5, wherein laminating includes melting.

7. The method of claim 6, wherein melting includes melting with a heat block.

8. The method of claim 6, wherein melting includes melting with an infrared sweep.

9. The method of claim 1, wherein mounting the sample on a surface includes mounting the sample on a glass slide.

10. The method of claim 1, wherein the barrier layer includes a polymer.

11. The method of claim 10, wherein said polymer includes ethyl vinyl acetate.

12. The method of claim 10, wherein said polymer includes polyester.

13. The method of claim 1, wherein the barrier layer includes paraffin.

14. The method of claim 1, wherein the barrier layer includes a solvent.

15. The method of claim 14, wherein the solvent includes xylene.

16. The method of claim 14, wherein the solvent includes cyclohexane.

17. The method of claim 1, wherein the barrier layer includes a dye.

18. The method of claim 1, further comprising laser capture microdissecting the sample.

19. The method of claim 1 further including the step of providing a removable layer coupled to the barrier layer.

* * * * *